United States Patent
Gloss et al.

(10) Patent No.: US 10,420,642 B2
(45) Date of Patent: Sep. 24, 2019

(54) TRANSCATHETER STENTED PROSTHETIC HEART VALVE DELIVERY DEVICES

(71) Applicant: Medtronic Vascular, Inc., Santa Rosa, CA (US)

(72) Inventors: Michael Gloss, Minneapolis, MN (US); Timothy Groen, Rush City, MN (US); Paul Rothstein, Elk River, MN (US); Jeffrey Sandstrom, Scandia, MN (US); Phil Haarstad, Minneapolis, MN (US); Joel Racchini, Edina, MN (US); Tuan Doan, Tempe, AZ (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 148 days.

(21) Appl. No.: 15/069,102

(22) Filed: Mar. 14, 2016

(65) Prior Publication Data
US 2017/0258587 A1  Sep. 14, 2017

(51) Int. Cl.
*A61F 2/24* (2006.01)

(52) U.S. Cl.
CPC .......... *A61F 2/2433* (2013.01); *A61F 2/2418* (2013.01); *A61F 2/2439* (2013.01); *A61F 2/2436* (2013.01); *A61F 2220/0033* (2013.01); *A61F 2220/0075* (2013.01); *A61F 2250/0047* (2013.01); *A61F 2250/0071* (2013.01)

(58) Field of Classification Search
CPC .................. A61F 2/2439; A61F 2002/9511
See application file for complete search history.

(56) References Cited

U.S. PATENT DOCUMENTS

| | | | |
|---|---|---|---|
| 5,035,706 A | 7/1991 | Giantureo et al. |
| 5,693,084 A | 12/1997 | Chuter |
| 5,776,186 A | 7/1998 | Uflacker |
| 6,280,465 B1 | 8/2001 | Cryer |
| 6,517,550 B1 | 2/2003 | Konya et al. |

(Continued)

FOREIGN PATENT DOCUMENTS

| | | |
|---|---|---|
| EP | 1842508 | 10/2007 |
| WO | WO2008/097590 | 8/2008 |
| WO | WO2016/183523 | 11/2016 |

OTHER PUBLICATIONS

PCTUS2017/022160, The International Search Report and the Written Opinion of the International Searching Authority, dated Jun. 23, 2017, 18pgs.

(Continued)

*Primary Examiner* — Shaun L David
(74) *Attorney, Agent, or Firm* — Dicke, Billig & Czaja, PLLC

(57) ABSTRACT

Disclosed embodiments and methods provide solutions for coupling and decoupling of a delivery device from a stented prosthetic heart valve with one or more release mechanisms. In situations when one or more sutures get tangled or caught upon attempted retraction of the delivery device and sutures after deployment of the stented prosthetic heart valve, a secondary release mechanism can be provided to sever the suture(s) or release the suture(s) from the delivery device. Exemplary secondary release mechanisms include high resistance inserts, cutters and balloon expandable devices. Methods of releasing the sutures from the delivery device or severing the suture(s) are also disclosed.

7 Claims, 8 Drawing Sheets

(56) References Cited

U.S. PATENT DOCUMENTS

| | | |
|---|---|---|
| 6,733,521 B2 | 5/2004 | Chobotov et al. |
| 6,740,111 B1 | 5/2004 | Lauterjung |
| 7,033,390 B2 | 4/2006 | Johnson et al. |
| 7,329,275 B2 | 2/2008 | Yee |
| 7,503,929 B2 | 3/2009 | Johnson et al. |
| 8,403,981 B2 | 3/2013 | Forster et al. |
| 2005/0119722 A1 | 6/2005 | Styrc et al. |
| 2007/0100427 A1* | 5/2007 | Perouse .................. A61F 2/07 623/1.11 |
| 2007/0203575 A1 | 8/2007 | Forster et al. |
| 2010/0049294 A1* | 2/2010 | Zukowski ............... A61F 2/954 623/1.11 |
| 2010/0286768 A1 | 11/2010 | Alkhatib |
| 2011/0040366 A1 | 2/2011 | Goetz et al. |
| 2012/0277734 A1 | 11/2012 | Goetz et al. |
| 2013/0197629 A1 | 8/2013 | Gainor et al. |
| 2013/0245752 A1 | 9/2013 | Goetz et al. |
| 2013/0338755 A1 | 12/2013 | Goetz et al. |
| 2014/0330368 A1 | 11/2014 | Gloss et al. |
| 2015/0112430 A1 | 4/2015 | Greaven et al. |
| 2015/0238315 A1 | 8/2015 | Rabito et al. |

OTHER PUBLICATIONS

U.S. Appl. No. 62/117,013, filed Feb. 17, 2015, Duffy et al.

* cited by examiner

TRANSCATHETER STENTED PROSTHETIC HEART VALVE DELIVERY DEVICES

BACKGROUND

The present disclosure relates to delivery devices, systems and methods for transcatheter implantation of a stented prosthetic heart valve. More particularly, it relates to delivery devices, systems and methods for ensuring that the delivery device can successfully be decoupled from the prosthetic heart valve for withdrawal from the patient.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other prosthetic heart valve designs, the stent frame is formed to be self-expanding. With these delivery devices, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a prosthetic valve is disclosed in U.S. Pat. No. 5,957,949 to Leonhardt et al., which is incorporated by reference herein in its entirety. After the prosthetic valve is in place and deployed, the delivery device is withdrawn from the patient.

SUMMARY

The disclosure relates to delivery devices, systems, and methods for delivery and deployment of a stented prosthetic heart valve. During delivery, the stented prosthetic heart valve is compressed onto an inner shaft assembly of the delivery device with one or more sutures. Tension in each suture can be released to allow the stented prosthetic heart valve to expand naturally. Once the stented prosthetic heart valve is in position and expanded, the sutures are released from the stented prosthetic heart valve and withdrawn from the patient, along with the delivery device. Sometimes, however, one or more sutures can get tangled or caught, thus prevent decoupling of the delivery device from the stented prosthetic heart valve. Disclosed embodiments and methods provide solutions for coupling and decoupling of the delivery device from the stented prosthetic heart valve. In certain embodiments, the sutures are releasable from the delivery device so that they are left entirely within the patient. Other disclosed embodiments are configured to sever the sutures so that a distal portion of each suture is left within the patient and a proximal portion of each suture is removed from the patient, along with the delivery device.

In various embodiments, each suture is connected to a primary release mechanism (e.g., a release pin) provided in the inner shaft assembly of the delivery device. The primary release mechanism can take a variety of configurations designed to allow for each suture to be entirely removed from the patient after deployment of the stented prosthetic heart valve. If the primary release mechanism fails to sufficiently enable withdrawal of the sutures, a secondary release mechanism can be used. In some embodiments, the secondary release mechanism is configured to detach each suture from the delivery device so that each entire suture is left within the patient with the stented prosthetic heart valve. In one demonstrative embodiment, the secondary release mechanism includes a cooperating pull pin and a retractable sleeve positioned within the inner shaft assembly to selectively retain and release the sutures as necessary. In other embodiments, the secondary release mechanism is configured to cut or otherwise sever the sutures into proximal and distal portions such that the respective proximal sections of the severed sutures can be withdrawn with the delivery device, leaving the respective distal portions of the severed sutures within the patient. Alternate disclosed features and methods for severing the sutures can include, but are not limited to, high resistance inserts for melting the sutures and balloons for forcibly expanding the sutures until they break.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" refer to a position distant from or moving in a direction away from the clinician. "Proximal" and "proximally" are a position near or moving in a direction toward the clinician. Although the present disclosure has been described with reference to preferred embodiments, workers skilled in the art will recognize that changes can be made in form and detail without departing from the spirit and scope of the present disclosure.

Figure 1:
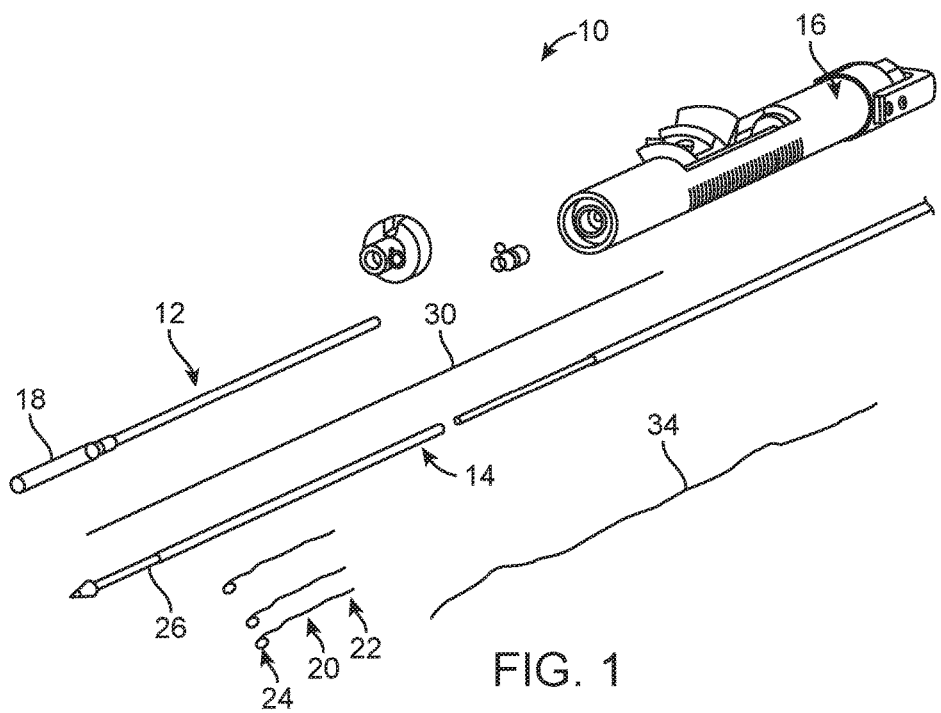
FIG. 1 is a perspective view of a delivery device for delivering a stented prosthetic heart valve (not shown).

As described below, aspects of the present disclosure relate to transcatheter stented prosthetic heart valve delivery devices utilizing one or more sutures to retain the stented prosthetic heart valve (hereinafter "prosthetic valve") in a compressed arrangement during delivery to a target site. By way of background, general components of one non-limiting example of a delivery device 10 are illustrated in FIGS. 1-2B. The delivery device 10 is arranged and configured for percutaneously delivering a prosthetic valve 40 to a patient's defective heart valve. The delivery device 10 includes an optional outer sheath assembly 12, an inner shaft assembly 14, and a handle assembly 16. Where provided, the optional outer sheath assembly 12 includes a capsule 18 selectively disposed over the prosthetic valve 40 that covers the prosthetic valve 40 for delivery and can be retracted by the handle assembly 16 to unsheathe the prosthetic valve 40 for deployment.

The delivery device 10 provides a loaded delivery state in which the prosthetic valve 40 is loaded over the inner shaft assembly 14 and is compressively retained on a spindle 26, or the like, by one or more sutures 20. Each of the sutures 20 include a first end 22 and a looped second end 24. The first end 22 is secured to a tensioning element 34 (e.g. a suture, wire, cable, or the like) that can be actuated with the handle assembly 16, for example, to adjust the tension on the sutures 20. Once the loaded and compressed prosthetic valve 40 is located at a target site, tension in the sutures 20 is lessened or released to permit the prosthetic valve 40 to self-expand, partially releasing and ultimately fully deploying the prosthetic valve 40 from the inner shaft assembly 14. The delivery device 10 can also include a primary release mechanism 30 (e.g., a pull pin or the like) for releasing the sutures 20 from the prosthetic valve 40.

Figure 2A:
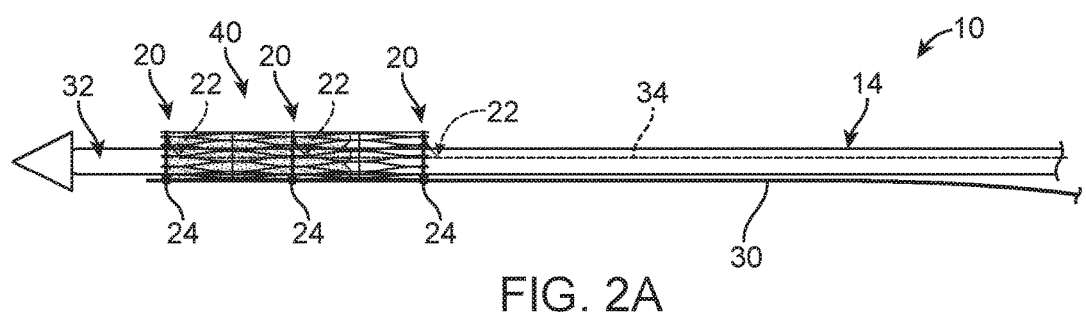
FIG. 2A is a partial, schematic illustration of the delivery device of FIG. 1 having the stented prosthetic heart valve compressively retained over the inner shaft assembly with a plurality of sutures; the delivery device further having a primary release mechanism positioned to retain the plurality of sutures around the stented prosthetic heart valve.
Figure 2B:
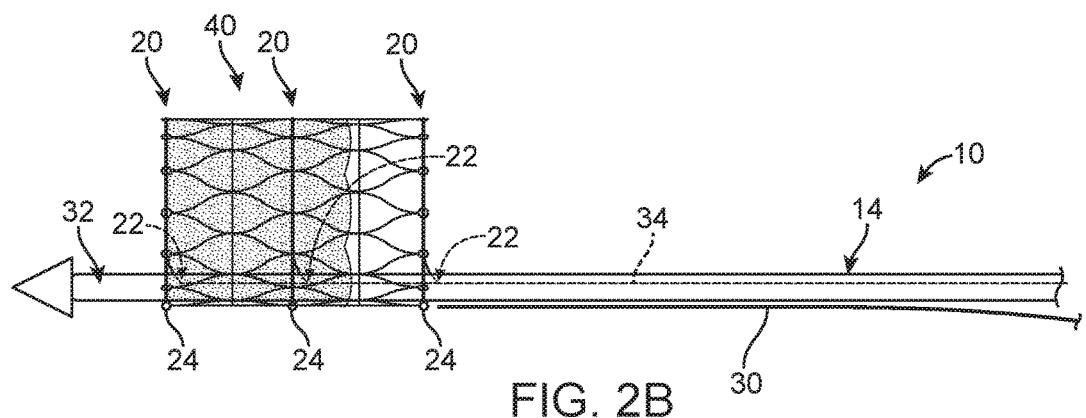
FIG. 2B is a partial, schematic illustration of the delivery device of FIGS. 1-2A having the stented prosthetic heart valve positioned over an inner shaft assembly; the stented prosthetic heart valve shown in an expanded arrangement and the primary release mechanism withdrawn to disengage the sutures.

FIGS. 2A-2B illustrate the primary release mechanism or pull pin 30, and tensioning element 34, in the assembled delivery device 10 (only part of the delivery device 10 is shown). As shown in FIG. 2A, when the prosthetic valve 40 is compressed with sutures 20 and loaded onto the spindle 26 for delivery, the pull pin 30 and the tensioning element 34 extend through a lumen 32 of the inner shaft assembly 14 (the inner shaft assembly 14 is illustrated as transparent in FIGS. 2A-2B for ease of illustration). The pull pin 30 is threaded through the looped second end 24 of each suture 20. When the tensioning element 34 is retracted proximally within the inner shaft assembly 14 to tension the sutures 20, the prosthetic valve 40 compresses in the compressed arrangement, as illustrated in FIG. 2A. When the tensioning element 34 is advanced distally to release tension in the sutures 20, the prosthetic valve 40 expands to the expanded arrangement, as illustrated in FIG. 2B. To facilitate release of the sutures 20 from the prosthetic valve 40, the pull pin 30 is retracted proximally to disengage the pull pin 30 from the second looped ends 24 of the sutures 20. Although the primary release mechanism or pull pin 30 is intended and designed to release the sutures 20, thus allowing the delivery device 10 to be fully disconnected from the prosthetic valve 40, sometimes the sutures 20 can become stuck or tangled. As further discussed below and illustrated in later figures, the present disclosure provides many embodiments in which the sutures 20 can be severed or otherwise disconnected with a secondary release mechanism so that the delivery device 10 can be safely withdrawn from the patient.

As referred to herein, stented prosthetic heart valves ("prosthetic valves") useful with the various delivery devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The prosthetic valves of the present disclosure may be self-expandable, balloon expandable, and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed arrangement for loading to the delivery device. For example, the stents or stent frames are support structures that comprise a number of struts or segments that are arranged relative to each other to provide a desired compressibility and strength to the prosthetic valve. The struts or segments are arranged such that they are capable of self-transitioning from, or being forced from, a compressed or collapsed arrangement to a normal, radially expanded arrangement. The struts or segments can be formed from a shape memory material, such as a nickel titanium alloy (e.g., Nitinol™). The stent frame can be laser-cut from a single piece of material, or can be assembled from a number of discrete components.

Figure 3:
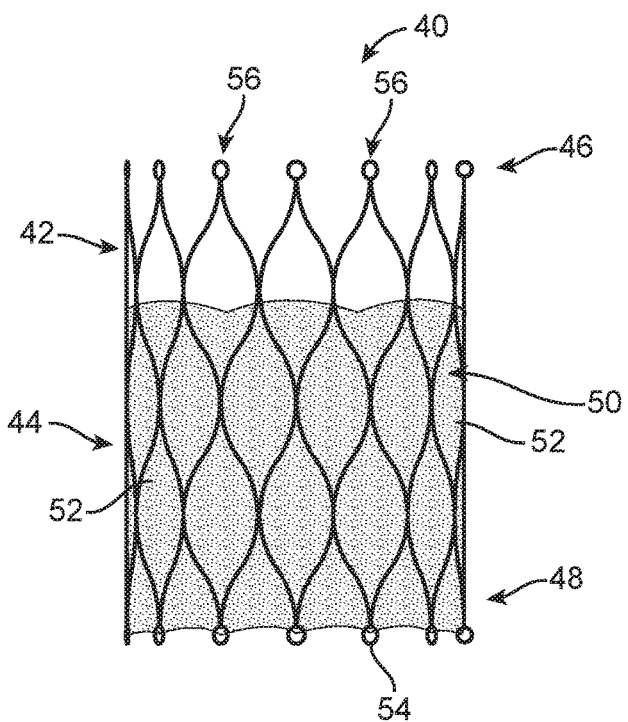
FIG. 3 is a perspective view of one illustrative stented prosthetic heart valve that can be used with the delivery devices disclosed herein.

One simplified, non-limiting example of the prosthetic valve 40 is illustrated in FIG. 3. As a point of reference, the prosthetic valve 40 is shown in a normal or expanded arrangement in this view. The prosthetic valve 40 includes a stent or stent frame 42 and a valve structure 44. The stent frame 42 has first and second ends 46, 48 and can assume any of the forms mentioned above, and is generally constructed to be self-expandable from the compressed arrangement to the normal, expanded arrangement.

The valve structure 44 of the prosthetic valve 40 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 44 can be formed, for example, from bovine, porcine, equine, ovine, and/or other suitable animal tissues. In some embodiments, the valve structure 44 can be formed, for example, from heart valve tissue, pericardium, and/or other suitable tissue. In some embodiments, the valve structure 44 can include or form one or more leaflets 50. For example, the valve structure 44 can be in the form of a tri-leaflet bovine pericardium valve, a bi-leaflet valve, or another suitable valve.

In some prosthetic valve 40 constructions, such as that of FIG. 3, the valve structure 44 can comprise two or three leaflets 50 that are fastened together at enlarged lateral end regions to form commissural joints, with the unattached edges forming coaptation edges of the valve structure 44. The leaflets 50 can be connected to the stent frame 42. As shown, the stent frame 42 can have a lattice- or cell-like structure, and optionally forms or provides posts 52 corresponding with commissures of the valve structure 44 as well as eyelets 54 or crowns 56 (or other shapes) at the first and second ends 46, 48. If provided, the posts 52 are spaced equally around the stent frame 42 (only one post 52 is visible in FIG. 3).

Figure 4A:
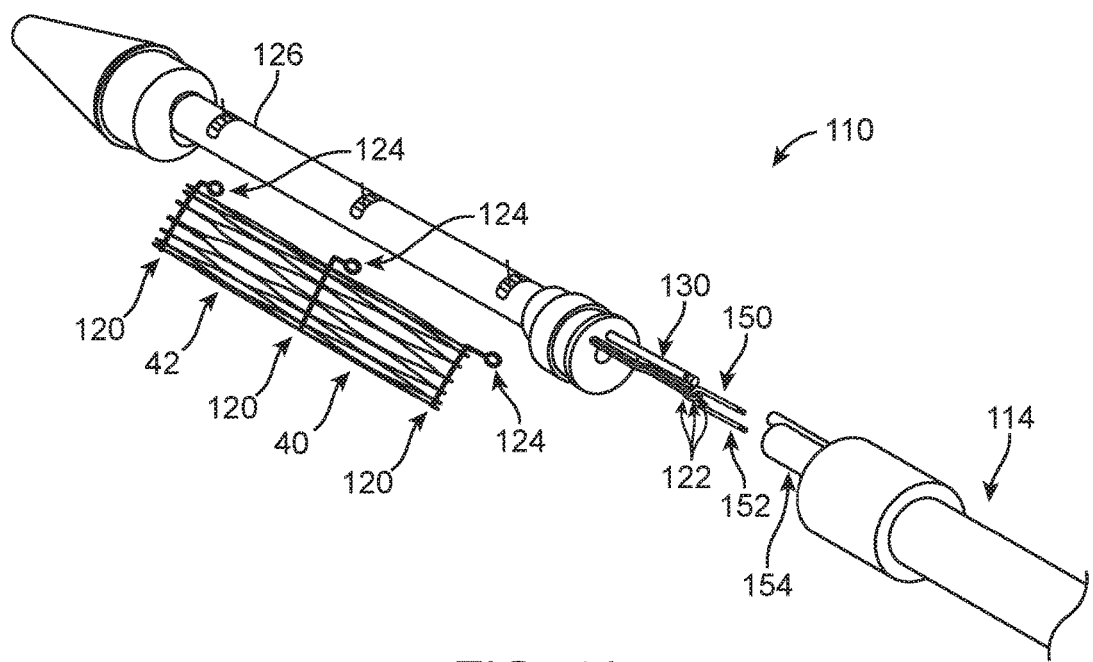
FIG. 4A is a partially exploded, perspective view of select components of an alternate delivery device having a primary release mechanism and a secondary release mechanism configured for complete separation of one or more sutures from the delivery device if the primary release mechanism is insufficient to enable withdrawal of the sutures.
Figure 4B:
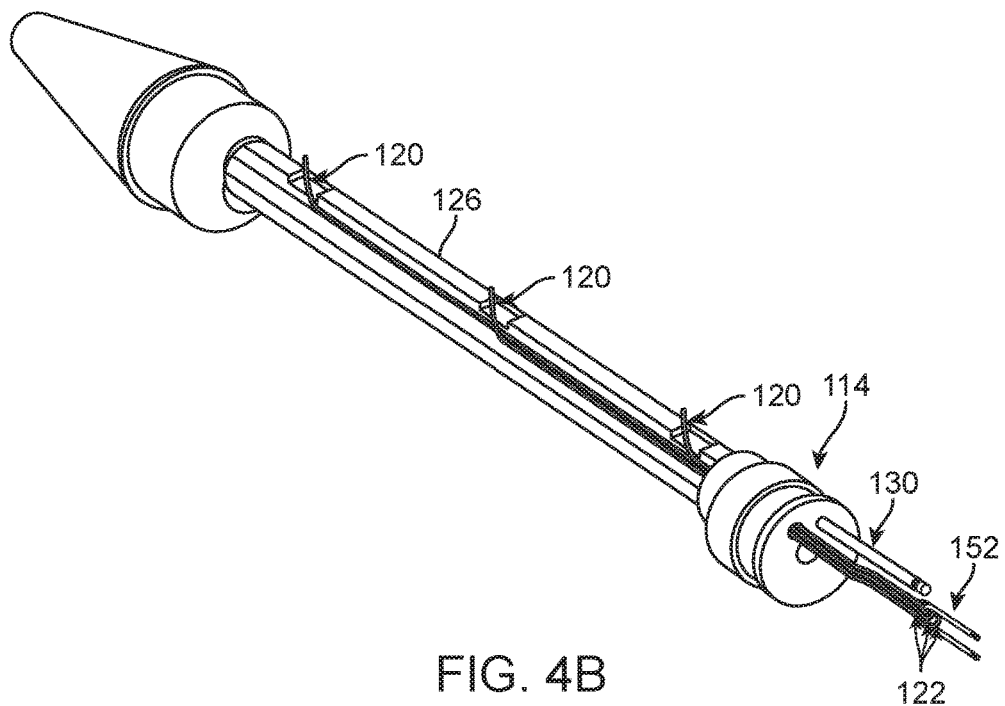
FIG. 4B is a partial, cross-sectional view of the delivery device of FIG. 4A illustrating the sutures (partially shown) operatively connected to a spindle and a high resistance insert of the secondary release mechanism.

FIGS. 4A-4E collectively illustrate select components of a delivery device 110, largely similar to the delivery device 10 of FIGS. 1-2B, except as indicated below. As shown in FIGS. 4A-4B, the delivery device 110 includes an inner shaft assembly 114 having a spindle 126 to which the prosthetic valve 40 can be secured with a plurality of sutures 120 (see also, FIGS. 2A-2B). Each suture 120 has first and second looped ends 122, 124, see also FIGS. 2A-2B which illustrate the looped second end 24 and how the second end 24 can be wrapped around the prosthetic valve 40 and connected to the pull pin 30. The first end 122 is fixedly secured and interconnected to a pull pin 156 that translates within the inner shaft assembly 114 to draw the sutures 120 proximally to compress the stent frame 42 and to draw the sutures 120 distally to release some tension on the sutures 120 to position the stent frame 42 in its expanded arrangement. Each looped second end 124 of the sutures 120 is releasably secured around a primary release mechanism or release pin 130, as discussed with respect to FIGS. 2A-2B. When the release pin 130 is retracted proximally, the second ends 124 disengage from the release pin 130 so that the sutures 120 can be released from the stent frame 42 and withdrawn from the patient with the delivery device 110.

Figure 4C:
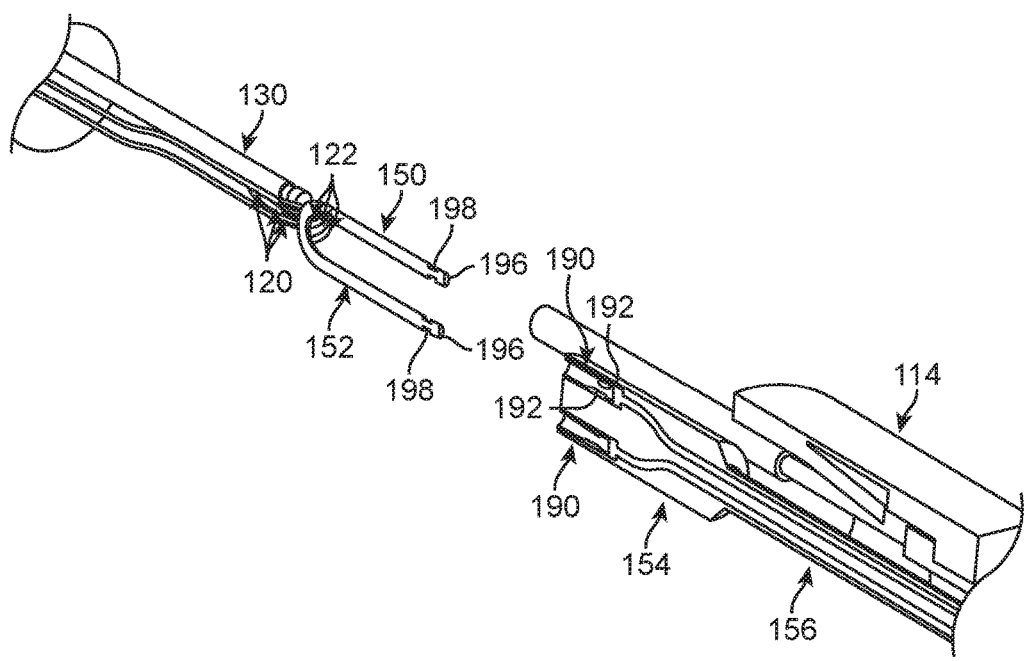
FIG. 4C is a cross-sectional view of the delivery device of FIG. 4A illustrating the high resistance insert and a connector of the secondary release mechanism.

In some instances, however, the sutures 120 become tangled or caught upon attempted withdrawal after release by the primary release mechanism 130. Therefore, the delivery device 110 further includes a secondary release mechanism 150 for severing the at least one suture 120 from the delivery device 110, should one or more of the sutures 120 get caught or otherwise become difficult to remove upon attempting withdrawal of the suture(s) 120 and the delivery device 110 from the patient. As illustrated in FIGS. 4A-4C, the first end 122 of each suture 120 is tied to a high resistance insert 152 of the secondary release mechanism 150. As discussed in further detail below, the high resistance insert 152 can be activated to melt each suture 120, thus allowing the delivery device 110 to break free from each suture 120 at the first end 122. In various embodiments, the high resistance insert 152 heats to a temperature between about 150 and 200 degrees C., which is generally sufficient for melting sutures made of polyethylene or nylon, for example.

To assemble the secondary release mechanism 150, one end 196 of the high resistance insert 152 is threaded through the looped first end 124 of each suture 120. The high resistance insert 152 is then snapped into a receiver 154 of a proximal end 158 of a pull pin 156 of the inner shaft assembly 114. The pull pin 156 is attached to a slider or other actuator (not shown) in the handle assembly for adjusting tension in the suture(s) 120 (also not shown, see handle assembly 16 of FIG. 1, for example). In one exemplary embodiment, the receiver 154 includes two connectors 190 that are over-molded with a non-conductive material. The pull pin 156 is constructed to include two insulated conductive wires 194 that extend a length of the pull pin 156 to the connectors 190. When the primary release mechanism 130 fails or is not provided, the secondary release mechanism 150 can be actuated by applying current to conductive wires 194 that cause the high resistance insert 152 to heat up to melt and disconnect the suture(s) 120 from the high resistance insert 152, and thus, disconnect the suture(s) 120 from the delivery device 110.

Figure 4D:
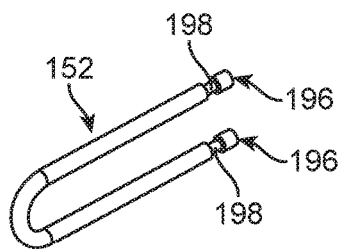
FIG. 4D is a perspective view of the high resistance insert of FIGS. 4A-4C.
Figure 4E:
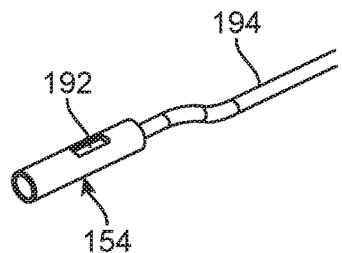
FIG. 4E is a partial, perspective view the connector configured to receive the high resistance insert of FIGS. 4A-4D.

As seen in FIG. 4D, the exemplary high resistance insert 152 is generally U-shaped, including two ends 196 that each have a stepped down section 198. The ends 196 are configured to snap into and be retained in two connectors 190 that are part of the pull pin 156. As best shown in FIG. 4E, the exemplary connectors 190 have one or more flexible tab features 192 to hold the high resistance insert 152 in place. The connectors 190 are electrically conductive and are attached to a conductive wire 194 via crimping, soldering, or the like.

Figure 5A:
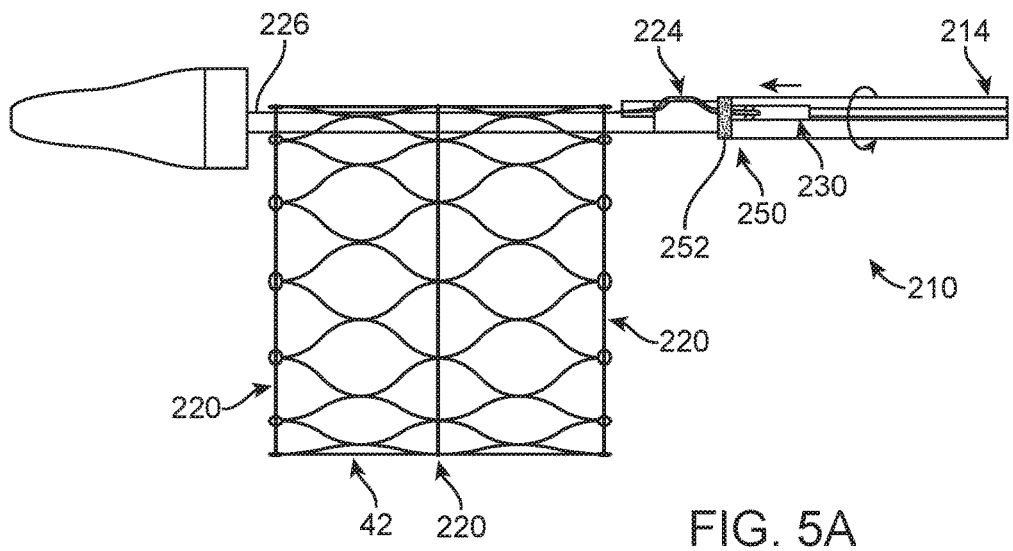
FIG. 5A is a partial, side view of an alternate delivery device having a secondary release mechanism including a spinning cutter that can be advanced to sever one or more sutures connecting the stented prosthetic heart valve to the delivery device.
Figure 5B:
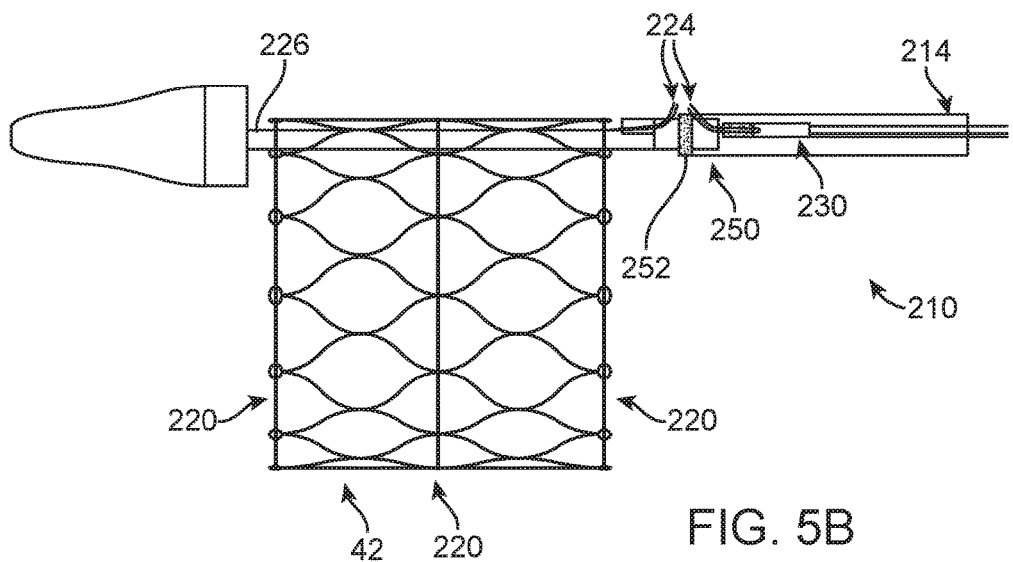
FIG. 5B is a partial, side view of the delivery device of FIG. 5A illustrating each suture having been severed by the spinning cutter.

Select portions of another delivery device 210 having a secondary release mechanism 250 are schematically illustrated in FIGS. 5A-5B. The delivery device 210 is similar to that of FIGS. 1-2B except as indicated below. The delivery device 210 includes an inner shaft assembly 214 having a spindle 216 on which the prosthetic valve 40 of FIG. 3 is attached (for ease of illustration, only the stent frame 42 of the prosthetic valve 40 of FIG. 3 is shown). The delivery device 210 includes a primary release mechanism 230 that is configured for retaining one end 222 of each suture 220 and releasably retaining a second end 224 of each suture 220 (the ends 222, 224 of only one suture 220 are labeled, again for ease of illustration). When the stent frame 42 is in the expanded arrangement at the target site and the delivery device 210 is to be disconnected from the stent frame 42, the primary release mechanism 230 releases the second end 224 of each suture 220 so that the suture 220 can be pulled off of the stent frame 42 and withdrawn from the patient along with the delivery device 210. As discussed above, the sutures 220 can become tangled, caught, or otherwise difficult to withdraw from the patient. Therefore, the delivery device 210 further includes a secondary release mechanism 250 for severing the at least one suture 220 from the delivery device 210, if necessary. In this embodiment, the secondary release mechanism 250 includes a spinning cutter 252 that can be advanced over and around the inner shaft assembly 214 to an exposed section 226 of each suture 220 to sever each suture 220 at the exposed section 226 upon contact. Two suitable spinning cutters are the TurboHawk™ (Super Cutter) Excision System and the SilverHawk™ Excision System available from ev3 of Plymouth, Minn., United States. In alternate embodiments, the secondary release mechanism 250 can be the only feature employed by the delivery device 210 to decouple the delivery device 210 from the stent frame 42.

Figure 6A:
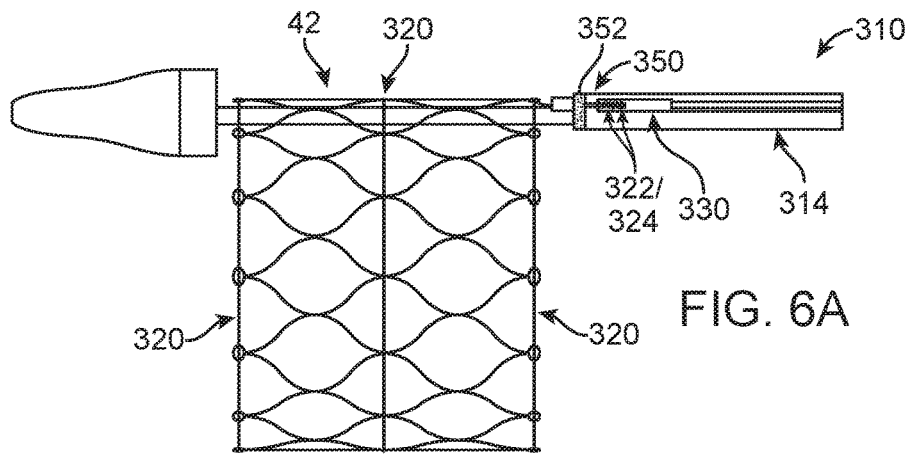
FIG. 6A is a partial, side view of an alternate delivery device having a secondary release mechanism including a spinning cutter that can be advanced across a stented prosthetic heart valve to sever one or more sutures connecting the stented prosthetic heart valve to the delivery device.
Figure 6B:
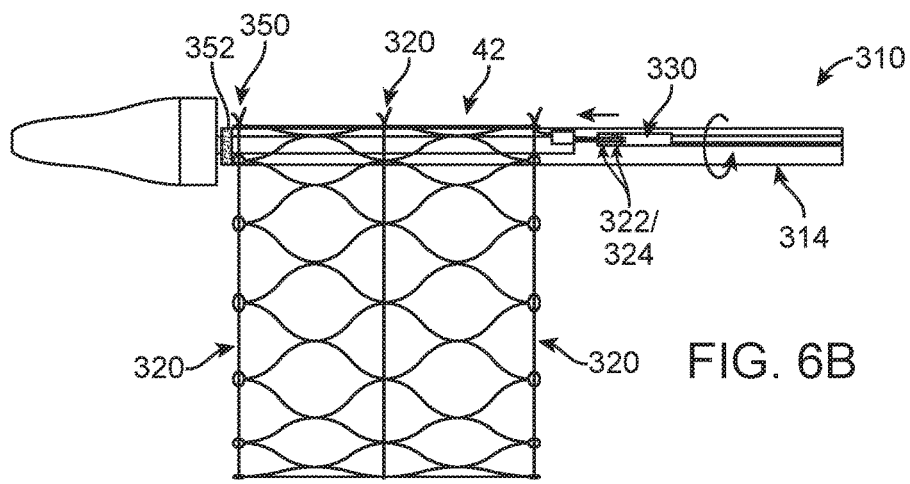
FIG. 6B is a partial, side view of the delivery device of FIG. 6A as the spinning cutter is advanced over the stented prosthetic heart valve.

Similarly, a delivery device 310 of FIGS. 6A-6B also includes a secondary release mechanism 350 including a spinning cutter 352, similar to those described above, positioned over and translatable over a length of an inner shaft assembly 314 (only part of the delivery device 310 is shown but the delivery device 310 is largely similar to that of FIGS. 1-2B except as indicated below). The delivery device 310 further includes a primary release mechanism 330 that is configured for retaining one end 322 of each suture 320 and releasably retaining a second end 324 of each suture 320 (the ends of only one suture 320 are labeled for ease of illustration). When the stent frame 42 is in the expanded arrangement at the target site and the delivery device 310 is to be disconnected from the stent frame 42, the primary release mechanism 330 releases the second end 324 of each suture 320 so that the suture 320 can be pulled off of the stent frame 42 and withdrawn from the patient along with the delivery device 310. As discussed above, the sutures 320 can become tangled or caught and difficult to withdraw from the patient. Therefore, the secondary release mechanism 350 serves as a backup release mechanism for severing the at least one suture 320 from the delivery device 310 should one or more of the sutures 320 get caught or otherwise difficult to remove upon attempting withdrawal of the suture(s) 320. In alternate embodiments, the secondary release mechanism 350 can be the only feature employed by the delivery device 310 to release the suture(s) 320 from the stent frame 42.

Figures 7A, 7B, 7C:
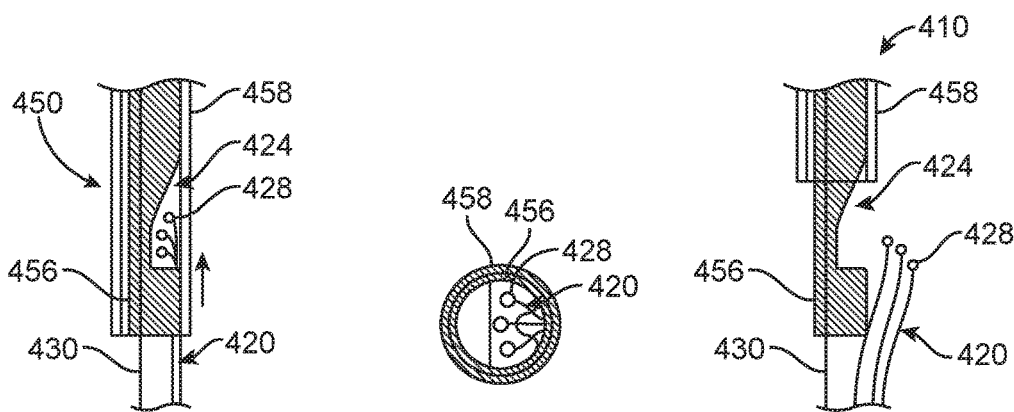
FIG. 7A is a partial, schematic illustration of select components of an alternate delivery device having a secondary release mechanism including a recess in which one or more sutures can be selectively retained.
FIG. 7B is a cross-sectional, schematic view of the secondary release mechanism of FIG. 7A illustrating the sutures secured within the recess.
FIG. 7C is a partial, schematic illustration of the delivery device of FIGS. 7A-7B in which a sleeve of the delivery device is retracted to release the sutures from the recess to disconnect the sutures from the delivery device.

FIGS. 7A-7C illustrate another delivery device 410 (only select portions of which are shown). The delivery device is similar to the delivery device 10 of FIGS. 1-2B, except as indicated below. The delivery device includes an inner shaft assembly 14 (see also FIGS. 1-2B and related disclosure), a pull pin 456, a sleeve 458 (shown as transparent in FIG. 7A for ease of illustration), and a primary release mechanism or release pin 430. The pull pin 456 actuates movement of, and thus tensioning of, the sutures 420 and the release pin 430 actuates release of the sutures 420 in relation to the prosthetic valve (not shown), in the same way as described with respect to the release pin 156 and the pull pin 130 of FIGS. 4A-4C. In this way, compression on the prosthetic valve is adjustable for delivery and deployment of the prosthetic valve. Once deployment of the prosthetic valve is complete, the sutures are to be released from the prosthetic valve and withdrawn from the patient along with the delivery device 410. If the primary release mechanism 430 is insufficient for releasing the sutures 420 from the prosthetic valve, the secondary release mechanism 450 is configured to disconnect the sutures 420 from the delivery device 410 so that the delivery device 410 can be removed from the patient.

The secondary release mechanism 450 is collectively formed by the pull pin 456 and the sleeve 458. The pull pin 456 defines a recess 424 in which one or more sutures 420 can optionally be secured. In this embodiment, each of the sutures 420 includes a retaining element 428 (e.g., a knot) that increases a diameter of the sutures 420 at a proximal end 426 to assist in maintaining the proximal end 426 of each suture 420 within the recess 424 when the sleeve 458 is positioned over the recess 424 (in FIGS. 7A-7C, only one suture 420 is labeled, for ease of illustration). Each suture 420 extends from out of the recess 424 to the prosthetic valve (not shown, see also FIGS. 2A-2B). As seen in FIG. 7B, the sleeve 458 is configured to fit closely over the pull pin 456 so that the sutures 420 cannot move out of the recess 424 when the retaining elements 428 are within the recess 424 and the sleeve 458 is positioned over the recess 424. To release the sutures 420, as shown in FIG. 7C, the sleeve 458 is retracted proximally to expose the recess 424, thus freeing the respective proximal ends 426 of the sutures 420 from the confines between the pull pin 456 and the sleeve 458 so that the delivery device 410 can be withdrawn from the patient, leaving the sutures 420 behind with the deployed prosthetic valve (not shown).

Figure 8A:
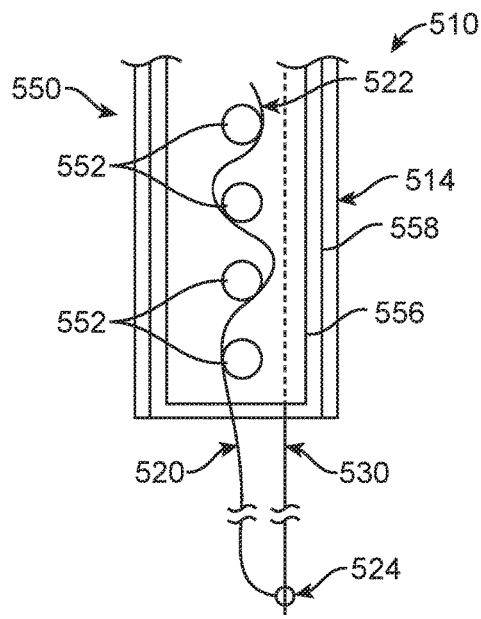
FIG. 8A is a partial, schematic illustration of select components of an alternate delivery device having a secondary release mechanism configured for optional, complete separation of one or more sutures from the delivery device.
Figure 8B:
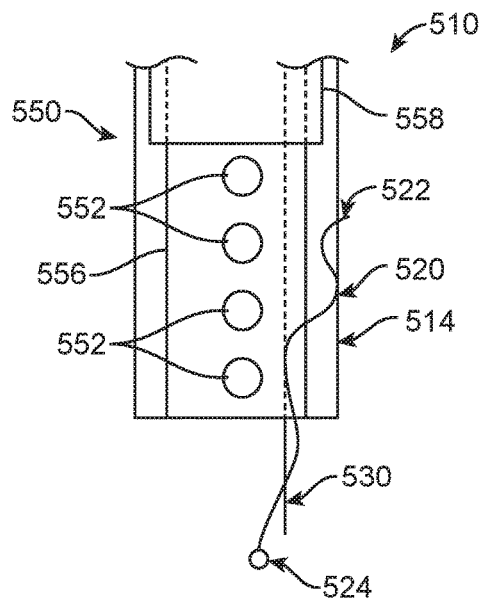
FIG. 8B is a schematic view of the delivery device of FIG. 8A illustrating that when a sleeve of the secondary release mechanism is retracted, each suture is disconnected from the delivery device.

FIGS. 8A-8B illustrate select components of another delivery device 510. The delivery device 510 is similar to the delivery device 10 of FIGS. 1-2B, except as indicated and includes, among other components, an inner shaft assembly 514 (shown as transparent for ease of illustration in FIG. 8A), a primary release mechanism or release pin 530, and a secondary release mechanism 550 defined by a pull pin 556 and a sleeve 558 (also shown as transparent for ease of illustration). The pull pin 556 actuates movement, and thus tensioning of the sutures 520 and the release pin 530 actuates release of sutures 520 in relationship to a prosthetic valve (not shown) in the same way as described with respect to the pull pin 156 and the release pin 130 of FIGS. 4A-4C. In this way, compression on the prosthetic valve is adjustable for delivery and deployment of the prosthetic valve. Once deployment of the prosthetic valve is complete, the sutures 520 are to be released from the prosthetic valve and withdrawn from the patient along with the delivery device 510. If the primary release mechanism or release pin 530 fails to sufficiently release the sutures 520 from the prosthetic valve, the secondary release mechanism 550 is configured to disconnect the sutures 520 from the delivery device 510 so that the delivery device 510 can be removed from the patient.

As with the embodiment of FIGS. 7A-7C, the sleeve 558 is configured to fit closely over the pull pin 556 so that each proximal end 522 of each suture 520 is secured to the delivery device 510. In this embodiment, the pull pin 556 includes a plurality of cleats 552 around which one or more sutures 520 is sinuously woven. When the sleeve 558 is positioned over the cleats 552, the suture(s) 520 is connected to the inner shaft assembly 514. Respective looped second ends 524 of each suture 520 are wrapped around the prosthetic valve and then threaded over the release pin 530. To release each suture 520 from the prosthetic valve, the release pin 530 is withdrawn to disengage from the looped distal ends 544 of each suture 520 so that the sutures 520 can be pulled off of the prosthetic valve and withdrawn from the patient, along with the delivery device 510. In some instances, the sutures 520 can get caught upon attempting withdrawal. Should the sutures 520 make withdrawal of the delivery device 510 difficult, the sleeve 558 of the secondary release mechanism 550 can be retracted proximally to expose the cleats 552, thus freeing the sutures 520 from being confined between the sleeve 558 and the pull pin 536, as shown in FIG. 8B. Each suture 520 is then released from the delivery device 510, which can then be withdrawn from the patient, leaving the suture(s) 520 behind with the prosthetic valve (not shown).

Figure 9A:
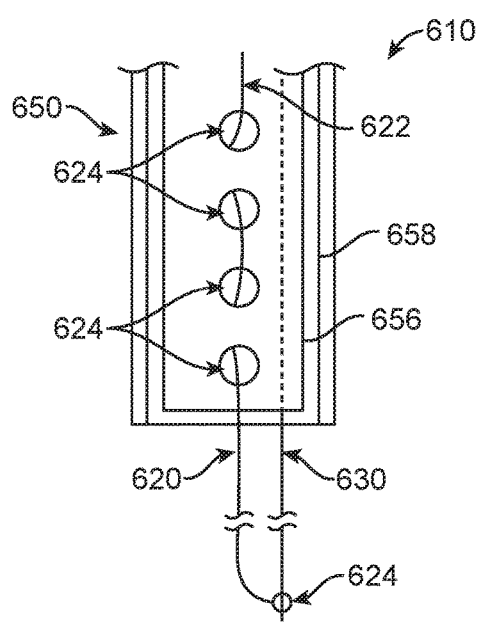
FIG. 9A is a partial, schematic illustration of select components of an alternate delivery device having a secondary release mechanism configured for optional, complete separation of one or more sutures from the delivery device.
Figure 9B:
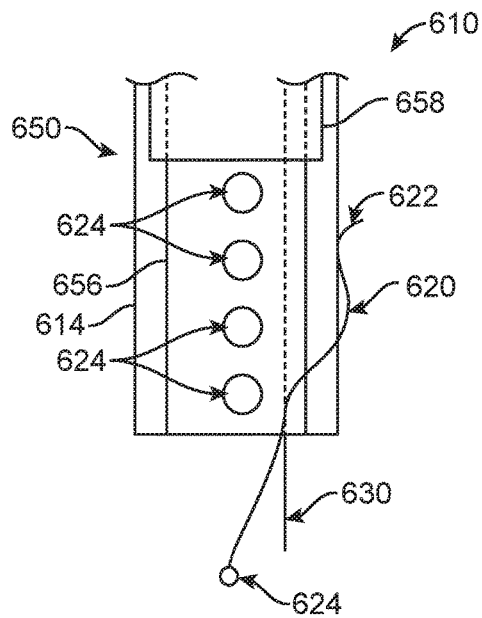
FIG. 9B is a schematic view of the delivery device of FIG. 9A illustrating that when a sleeve of the secondary release mechanism is retracted, each suture is released from the delivery device.

Similarly, select components of an alternate delivery device 610 are schematically illustrated in FIGS. 9A-9B. The delivery device 610 is similar to the delivery device 10 and 510 of FIGS. 1-2B and 8A-8B, except as indicated and includes, among other components, an inner shaft assembly 614 (shown as transparent for ease of illustration in FIG. 9A), a primary release mechanism or release pin 630, and a secondary release mechanism 650 collectively formed by a pull pin 656 and a sleeve 658 (also shown as transparent for ease of illustration). The primary release mechanism, or release pin 630, actuates movement and the release of one or more sutures 620 in relation to a prosthetic valve (not shown) in the same way as described with respect to FIGS. 2A-2B. The secondary release mechanism 650 is collectively formed by the pull pin 656 and sleeve 658. For example, to prepare the delivery device 610 for delivery of a prosthetic valve (not shown), respective first ends 622 of one or more sutures 620 are woven through a plurality of apertures 652 and then the sleeve 658 is positioned distally over the apertures 652 as illustrated in FIG. 9A. As with the embodiments of FIGS. 7A-8B, the sleeve 658 is configured to fit closely over the pull pin 656 so that each first end 622 or each suture 620 is secured to the delivery device 610. Respective looped second ends 624 of each suture 520 are wrapped around the prosthetic valve and then threaded over the release pin 530 (see also, FIGS. 2A-2B, for example). To release each suture 620 from the prosthetic valve, the release pin 630 is withdrawn to disengage from the looped second ends 624 of each suture 620 so that the sutures 620 can unwrap from the prosthetic valve and be withdrawn from the patient, along with the delivery device 610. In some instances, the sutures 620 can get caught upon attempting withdrawal. Therefore, the secondary release mechanism 650 is provided. Should the sutures 620 make withdrawal of the delivery device 610 difficult, the sleeve 658 of the second release mechanism 650 can be retracted proximally to expose the apertures 652, thus freeing the sutures 620 from being confined within the apertures 652 as generally shown in FIG. 9B. Each suture 620 is then released from the delivery device 610, which can then be withdrawn from the patient, leaving the suture(s) 620 behind with the prosthetic valve (not shown).

Figure 10A:
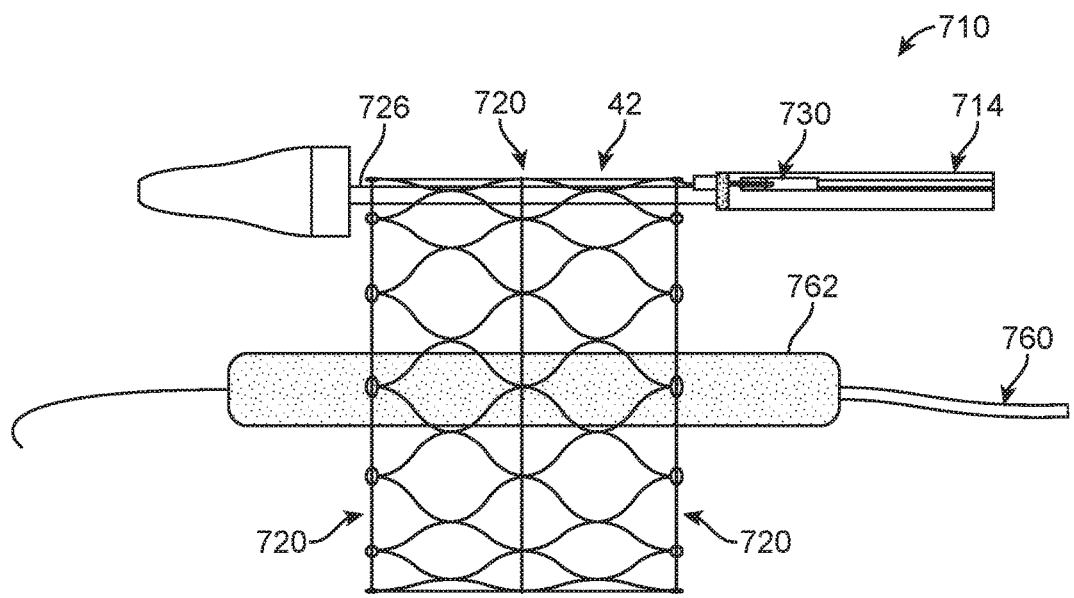
FIG. 10A is a partial, schematic illustration of a delivery device having a secondary release mechanism including a balloon capable of severing one or more sutures positioned around a stent frame so that the delivery device can be withdrawn from the patient.
Figure 10B:
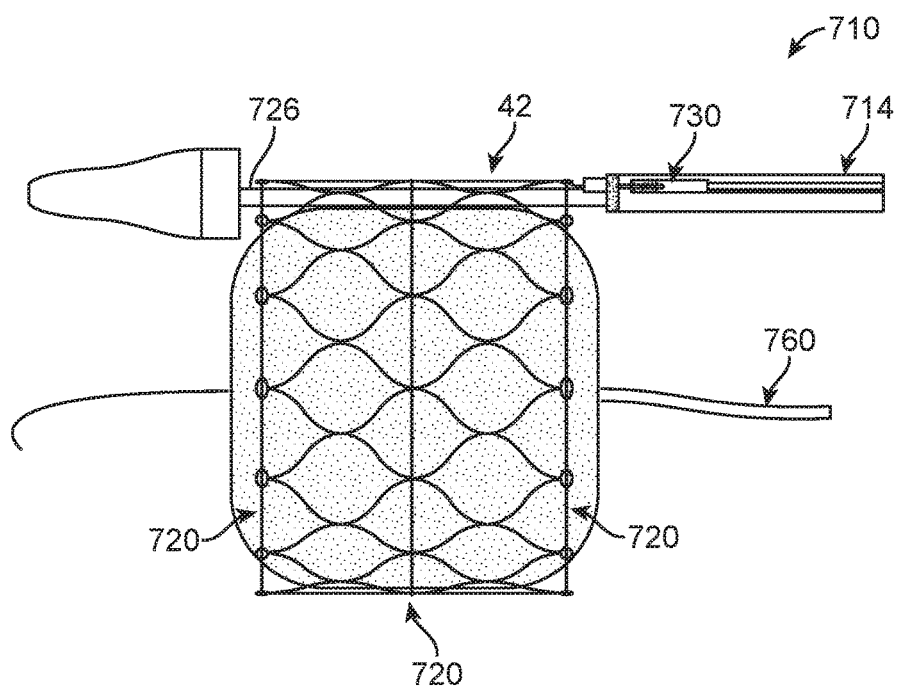
FIG. 10B is a partial, schematic illustration of the balloon of FIG. 10A inflated to sever the sutures surrounding the stent frame.
Figure 10C:
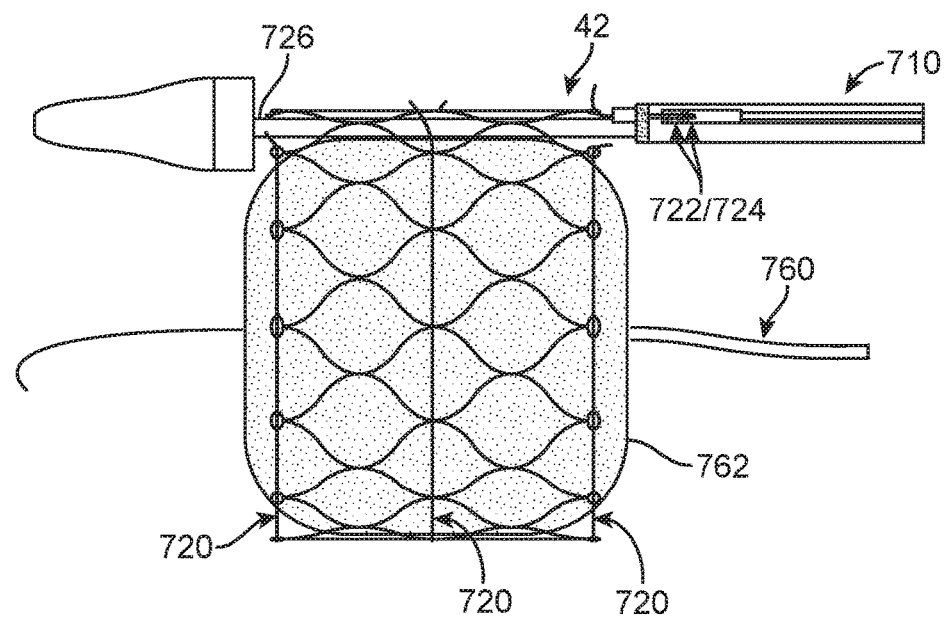
FIG. 10C is a partial, schematic illustration of the sutures of FIGS. 10A-10B having been severed by the inflated balloon.

In yet a further embodiment illustrated in FIGS. 10A-10C, a delivery device 710, largely similar to the delivery device 10 of FIGS. 1-2B, includes an inner shaft assembly 714 having a spindle 726 on which the prosthetic valve 40 of FIG. 3 is positioned (only the stent frame 42 of the prosthetic valve 40 is shown for ease of illustration). A plurality of sutures 720 are positioned around the stent frame 42 for selectively compressing and expanding the stent frame 42 as discussed with respect to FIGS. 2A-2B. The sutures 720 extend around the stent frame 42 and then to the inner shaft assembly 714 to a primary release mechanism 730. The primary release mechanism 730 is configured for retaining one end 722 of each suture 720 and releasably retaining a second end 724 of each suture 720 (the ends of only one suture 720 are labeled for ease of illustration). When the stent frame 42 is in the expanded arrangement at the target site and the delivery device 710 is to be disconnected from the stent frame 42, the primary release mechanism 730 releases the second end of each suture 720 so that the suture can be pulled off of the stent frame 42 and withdrawn from the patient along with the delivery device 710. As discussed above, sutures 720 can become tangled or caught and difficult to withdraw from the patient. Therefore, the delivery device 710 is further accompanied with a secondary release mechanism catheter 760 having a balloon 762 that can be inserted through the stent frame 42. To release one or more sutures 20 from the stent frame 42 (here, three sutures 20 are provided), each suture 20 is at least partially tensioned with the delivery device 10 to slightly compress the stent frame 42 while the balloon 762 is inflated. Pressure is thus placed on each suture 20 with the expansive force of the balloon 762 until each suture 20 snaps and breaks. Each proximal end 24 of the respective sutures 20, proximal to the point of fracture, is then retracted with the delivery device 10, which is freed from the stent frame 42. The distal end 26b of each suture 20 is left behind with the stent frame 42. In this embodiment, the suture 20 break or fracture force is configured to be less than any of the other delivery device 10 break forces proximal to the stent frame 42. In this embodiment, if an over-crimping prevention feature (not shown) is provided in the handle assembly 16, such as a torque slip, the crimping prevention feature is disabled during the step of breaking the suture(s) 20. It will be understood that the secondary release mechanism catheter 760 of FIGS. 10A-10C can be provided and used with delivery devices other than the specific delivery devices illustrated in FIGS. 1-10C.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthetic heart valve to a native heart valve; the delivery device comprising:
   an inner shaft assembly on which the prosthetic heart valve can be releasably connected in a loaded state with a suture having a first end and a second end;
   a primary release mechanism including a pin engaged with the first end of the suture configured for attempted release of the suture from the stented prosthetic heart valve; and
   a secondary release mechanism engaged with the second end of the suture and configured to release the suture from the delivery device;
   wherein the secondary release mechanism includes a sleeve that can be positioned to selectively retain and release the suture from the delivery device and the secondary release mechanism includes a pull pin; wherein the pull pin can adjust tension on the suture; further wherein the pull pin defines a recess in which the suture can be positioned; wherein, in one position the sleeve is positioned over the recess to secure the suture within the recess and, in a second position, the sleeve is retracted proximally to release the suture from the recess.

2. The delivery device of claim 1, wherein the second end comprising a retaining element and the first end comprising a loop.

3. The delivery device of claim 2, wherein the retaining element comprises a knot.

4. The delivery device of claim 1, comprising two sutures, wherein the sleeve can be positioned to selectively retain and release one respective end of each suture.

5. The delivery device of claim 4, comprising three sutures.

6. The delivery device of claim 1, wherein the sleeve is configured to be positioned over the pull pin in the loaded state.

7. The delivery device of claim 1, wherein the recess is provided in an outer circumference of the pull pin.

* * * * *